(12) United States Patent
Licher et al.

(10) Patent No.: US 8,546,102 B2
(45) Date of Patent: Oct. 1, 2013

(54) METHODS FOR DETERMINING SODIUM-PROTON-EXCHANGER LIGAND EFFICIENCY

(75) Inventors: Thomas Licher, Frankfurt am Main (DE); Hans-Willi Jansen, Frankfurt am Main (DE); Ursula Schindler, Bad Soden (DE); Stefan Schaefer, Goch (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/063,497

(22) PCT Filed: Sep. 25, 2009

(86) PCT No.: PCT/EP2009/062428
§ 371 (c)(1),
(2), (4) Date: Jul. 15, 2011

(87) PCT Pub. No.: WO2010/034801
PCT Pub. Date: Apr. 1, 2010

(65) Prior Publication Data
US 2011/0262955 A1    Oct. 27, 2011

(30) Foreign Application Priority Data

Sep. 26, 2008  (EP) .................................... 08290916
Jan. 12, 2009  (EP) .................................... 09290028

(51) Int. Cl.
*C12Q 1/02*    (2006.01)
(52) U.S. Cl.
USPC ........................................................ 435/29
(58) Field of Classification Search
USPC ........................................................ 435/29
See application file for complete search history.

(56) References Cited

U.S. PATENT DOCUMENTS

| 5,334,507 A | 8/1994 | Soya et al. |
| 5,501,958 A | 3/1996 | Berry et al. |
| 5,719,036 A | 2/1998 | Tadano et al. |

FOREIGN PATENT DOCUMENTS

| WO | WO 02/14475 A2 | 2/2002 |
| WO | WO 2005/059101 A2 | 6/2005 |

OTHER PUBLICATIONS

Hillebrand U. et al. 17 beta Estradiol Increases Volume . . . Cardiovascular Research 69:916-924, 2006.*
Orlowski J. et al. Diversity of the Mammalian Sodium/Proton Exchanger SLC9 Gene Family. European J Physiology 447:549-565, 2004.*
Dhein S. et al. Na+/H+ Exchange Inhibition by Cariporide. Cardiovascular Drug Reviews 17(2)134-146, 1999.*
International Search Report—WO2010/034801 dated Apr. 1, 2010.
Franchi et al., Functional expression of a human Na+/H+ antiporter gene transfected into antiporter-deficient mouse I. cells, Proc. Natl. Acad. Sci vol. 83, Dec. 1986, pp. 9388-9392.
Netzer et al, HTS techniques to investigate the potential effects of compounds on cardiac ion channels at early-stages of drug discovery, Current Opinion in Drug Discovery and Development, Current Drugs, vol. 6, No. 4, Jul. 1, 2003, pp. 462-469.
Schwark et al., S3226, a novel inhibitor of Na+/H+ exchanger subtype 3 in various cell types, Pflugers Arch—Eur J Physiol, 1998, vol. 436, pp. 797-800.
Wiemann et al., Selective inhibition of the Na+/H+ exchanger type 3 activates CO2/H+-sensitive medullary neurones, Pflugers Arch—Eur J. Physiol. 1999, vol. 438, pp. 255-262.
Ahmad, Arylcyclopropanecarboxyl Guanidines as Novel, Potent, and Selective Inhibitors of the Sodium Hydrogen Exchanger Isoform-1, J. Med. Chem, 2001, 44, pp. 3302-3310.
Lang, Plasma from Myasthenia Gravis Patients Reduces Acetylcholine Receptor Agonist-Induced Na+ Flux into TE671 Cell Line, Journal of Neuroimmunology, 19, (1988), pp. 141-148.

* cited by examiner

*Primary Examiner* — Ralph Gitomer
(74) *Attorney, Agent, or Firm* — Lathrop & Gage LLP; James H. Velema, Esq.

(57) ABSTRACT

The present invention relates to methods for determining the in vivo efficiency of a sodium-proton-exchanger (NHE) ion channel ligand comprising the steps of: (a) contacting a cell expressing a sodium-proton-exchanger (NHE) ion channel in vitro with either (i) plasma of an animal and the ion channel ligand or (ii)) the plasma of an animal which has been administered the ion channel ligand; (b) determining the effect of the ion channel ligand on the cell; c) determining ion channel ligand availability by comparing the ligand concentration in the plasma to the concentration of ligand administered; and d) correlating the effect of the ion channel ligand on the cell with the ligand availability to determine the in vivo efficiency of the ligand.

18 Claims, 2 Drawing Sheets

METHODS FOR DETERMINING SODIUM-PROTON-EXCHANGER LIGAND EFFICIENCY

This application is a National Stage application filed under Rule 371 based on PCT/EP2009/062428 filed Sep. 25, 2009, which claims priority to EP 09290028.1 filed Jan. 12, 2009 which claims priority to EP 08290916.9 filed Sep. 26, 2008.

The present invention relates to methods for determining the efficiency of an ion channel ligand.

The $Na^+/H^+$-exchanger or sodium-proton-exchanger (NHE) family of membrane transporters utilizes the extra-to-intracellular $Na^+$ gradient to drive $H^+$ efflux from cells. Amongst the essential functions performed by these groups of transporters (or ion channels) are the regulation of cell volume and pH, a permissive role in cell proliferation and a trans-epithelial transport of $Na^+$. The mammalian NHE is an integral membrane protein that functions to exchange one intracellular proton for one extracellular sodium ion. By its involvement in ion fluxes, NHE serves to regulate intracellular pH and cell volume, and to initiate changes in the growth or functional state of cells. Aside from its physiological role, NHE serves important roles in human pathology. Transport by NHE plays a pivotal role in the damage caused to the human myocardium during and following a myocardial infarction and it is considered to represent a key step in the oncogenic transformation of cancerous cells. Therefore, NHEs have been a target in the cardiovascular and oncogenic research for a number of years and thousands of compounds have been screened for NHE inhibition and selectivity.

The standard method to determine potency of NHE antagonists is an in vitro assay described by Schwark and co-workers (Schwark et al., 1998, Pflügers Arch., 336(5):797-800) and Wiemann and co-workers (Wiemann et al., 1999, Pflügers Arch., 436(3):255-262). After determination of the $IC_{50}$ of the ligand on the NHE of choice, the selectivity against other NHEs may be measured with the same assay. In general, potent ligands with good selectivity were selected for further investigation by pharmacokinetics, in vivo proof of ligand etc. However, some very potent compounds showed only slight effects in in vivo studies. The reasons could be a high protein binding, a low bioavailability or other effects decreasing the effective concentration of compounds in blood plasma. It is desirable to exclude those compounds very early in the drug development process in order to save time and resources.

Due to the discrepancy between the in vitro $IC_{50}$ and the pharmacological potency (efficiency) of several compounds, there was a need to develop a method for determining or simulating the efficiency of NHE ligands or ligands of other ion channels in the body.

Accordingly, it was the first object of the present invention to provide a method for determining ion channel ligand efficiency. Preferably, this test should be time- and cost-effective. In the context of this application, the term ion channel is understood to comprise passive ion channels as well as active ion channels (ion transporters).

Surprisingly, it was found that the efficiency of ion channel ligands, particularly NHE antagonists, may be determined by contacting a cell expressing the ion channel with plasma of an animal and the ion channel ligand. In this test, it was possible to determine the effect of the ion channel ligand on the cell, wherein this effect reflects in vivo efficiency of the ligand.

Accordingly, in a first aspect the present invention provides a method for determining the efficiency of an ion channel ligand comprising the steps of:

a) contacting a cell expressing the ion channel with
   i) plasma of an animal and
   ii) the ion channel ligand; and
b) determining the effect of the ion channel ligand on the cell.

In brief, the method may be carried out as follows: A suitable cells expressing the ion channel in question is maintained (e.g. cultured) under suitable conditions and contacted (incubated) with the plasma of an animal and the ion channel ligand. Both components may be added simultaneously or concurrently. After a time sufficient to allow for an effect on the cell, the effect on the cell is determined. After or simultaneously with the contacting, an effect (signal) is observed, wherein the detection of an effect is indicative of the effect of the ion channel ligand on the cell.

The term "efficiency of an ion channel ligand" in the context of the present invention relates to the pharmacological potency of an ion channel ligand. In contrast to in vitro assay in the absence of plasma, the method of the invention carried out in the presence of plasma accounts for the quantity of protein binding, extent and rate of absorption, distribution, metabolism and excretion of the ligand availability and/or other effects decreasing the effective concentration of compounds in blood plasma. When the ligand has been administered to an animal and plasma is taken from the animal, the method also accounts for extent and rate of absorption, distribution, metabolism and excretion of the ligand. These effect may depend without limitation on the physical properties of the drug (hydrophobicity, pKa, solubility), drug formulation, administration in a fed or fasted state, circadean characteristics and/or interaction with other drugs, food or endogenous substances (e.g. enzymes). Accordingly, the term "efficiency of an ion channel ligand" relates not only to the binding of the ligand to the ion channel and the induction of the downstream signal transduction, but also accounts for the above effects of the ligand in plasma and/or the living animal. This allows for more convenient identification of suitable drug candidates e.g. for in vivo therapy and/or exclusion of compounds with low in vivo efficiency.

Effect of the ligand on the cell may be any effect on the cell, including without limitation altered morphology, viability or composition of intracellular compounds. The effect may be at any level of the signal transduction of the ion channel including binding of ligand to the ion channel, the flux of the ion, the binding of a respective ion to a target such as an intracellular target, the determination of the amount of a cellular compound such as a second messenger (e.g. cAMP, cGMP, $Ca^{2+}$, $IP_3$, diacylglycerol etc.), the determination of the activation state of an intracellular protein such as protein kinase A, protein kinase C, or a MAP kinase, the determination of the amount of mRNA or a protein, any altered cell function (such as induction of apoptosis or cell circle arrest) etc.

This method may be used in order to determine or simulate the ion channel's ligand efficiency in vivo. Examples of the range of application of the method include the following:

First, the effective concentration of ion channel ligands in a plasma sample derived from animals administered with ion channel ligands may be measured (see for example Example 2). If the ligand is administered to an animal, low ligand plasma concentrations in comparison to administered amount of ligand may be interpreted as poor bioavailability (e.g. due to low plasma half-time).

Second, the effect of the ion channel ligand in plasma, such as human plasma, may be determined (see for example Example 2). In comparison to $IC_{50}$ measured in a plasma-free assay (as known in the art), it is possible to draw conclusions to plasma binding and in vivo availability of the ligand. Compounds with a very high difference in the $IC_{50}$ and effeciency in plasma could be discarded earlier and so there is a potential for cost saving in drug development. At present, these compounds can only be rejected after in vivo experiments.

An ion channel is a protein, in general pore-forming, that helps to establish and control the flow of ions across the plasma membrane. It is an integral protein or, more typically, an assembly of several proteins. Such multi-subunit assemblies usually involve a circular arrangement of identical or homologous proteins closely packed around a water-filled pore through the plasma membrane. While some channels permit the passage of ions based solely on charge, the archetypical channel pore is just one or two atoms wide at its narrowest point. It conducts a specific species of ions, such as sodium or potassium, and conveys them through the membrane. In some ion channels, passage through the pore is governed by a "gate" which may be opened or closed by chemical or electrical signals, temperature, or mechanical force, depending on the variety of the ion channel.

Usually, ion channels are specified depending on the gating, the species of the ions passing through those gates and the number of pores.

If classified by the gating, channels are divided into two classes, voltage-gated ion channels (activation/inactivation depending on the voltage gradient across the membrane) and ligand-gated ion channels (activation/inactivation depending on binding of a ligand to the channel).

Examples of voltage-gated channels include voltage-gated sodium channels, voltage-gated calcium channels, voltage-gated potassium channels, some transient receptor potential channels, hyperpolarization-activated cyclic nucleotide-gated channels and voltage-gated proton channels. Examples of ligand-gated channels include potassium channels, such as inward-rectifier potassium channels, calcium-activated potassium channels and two-pore-domain potassium channels, light-gated channels like channel rodopsin and cyclic nucleotide-gated channels. When classified by the ions passing through the channels, ion channels are in general classified as follows:

Chloride channels, potassium channels, such as voltage-gated potassium channels, calcium-activated potassium channels, inward rectifier potassium channels and two-pore-domain potassium channels, sodium channels, calcium channels, proton channels, such as voltage-gated proton channels and general ion channels being relatively non-specific or ions including most transient receptor potential channels.

Some ion channels influence intracellular pH, like the Sodium Bicarbonate Cotransporter and the sodium proton exchanger (NHE). The activity of ion channels may be influenced by natural or non-natural occurring ligands which bind to the ion channels in question. Well-known examples of those include tetrodotoxin, saxitoxin, lidocain and novocain blocking sodium ion channels as well as dendrotoxin, iberiotoxin and heteropodatoxin blocking potassium channels.

In accordance with this, an ion channel ligand is any chemical which binds specifically to an ion channel. "Specifically binding to an ion channel" according to the present invention includes, without limitation, binding with a dissociation constant $K_D$ of not exceeding $10^{-4}$ mol/l, preferably not exceeding $10^{-5}$ mol/l. The dissociation constant $K_D$ may be determined in e.g. competition binding experiments as well-known to the skilled person according to the following equation:

$$B[L]=[L]/\{[L]+K_{DL}(1+[L^*]/K_{DL^*}\},$$

wherein [L] and [L*] represent the concentration of the ion channel ligand in question and the concentration of a detectable (e.g. labeled) ion channel ligand, such as a radioligand for the ion channel, respectively. $K_{DL}$ and $K_{DL^*}$ are the dissociation constants of the ion channel ligand in question and the detectable ligand, respectively, and B[L] (from 0% to 100%) is the binding at a particular concentration of the ion channel ligand.

In a preferred embodiment of the invention the ligand to be identified is an agonist or an antagonist. Agonists bind to the ion channel and activate it (e.g. by inducing a conformational change). Antagonists or blockers also bind to the ion channel and inactivate it. Activation and inactivation may lead to detectable signal, if the state (active or inactive) of the ion channel is changed by the ligand. Preferably, the ligand is an antagonist inactivating the ion channel in question. The ligand characterized by the method of the invention can be used as potential drug useful in treatment and prevention of ion channel-related disorders or diseases.

In a preferred embodiment of the invention the ion channel is a Sodium-Proton-Exchanger (NHE) or a Sodium-Bicarbonate-Cotransporter. Since the structure of a protein such as an enzyme which functions in cells is greatly affected by pH, there is an optimal pH for the protein function. For that reason, maintenance and regulation of an intracellular pH is extremely important to cells for maintaining homeostasis of the cellular function. NHE as well as Sodium-Bicarbonate-Cotransporter are involved in the regulation of a cell's pH. A Sodium-Bicarbonate-Cotransporter is driven by the concentration gradient of $Na^+$ inside and outside a cellular membrane, and take one $Na^+$ into a cell together with one or more $HCO_3^-$ ions. Since a Sodium-Bicarbonate-cotransporter exists in the cell membrane and $HCO_3^-$ taken into cells by a Sodium-Bicarbonate-cotransporter neutralizes $H^+$ in the cytoplasma, it plays an important role in regulating an intracellular pH.

Also NHEs play an important role in the regulation of intracellular pH. To date, nine isoforms (NHE1 to NHE9) have been identified within the mammalian NHE family. The isoforms share approx. 25 to 70% sequence identity, with calculated relative molecular masses ranging from approx. 74000 to 93000. Structural analysis of the exchangers suggests that they have similar membrane topologies, with an amino-terminal membrane domain consisting of twelve transmembrane segments and a more divergent carboxy-terminal cytoplasmic domain.

It has long been known that NHE is important for tumour growth, because tumour cells deficient in $Na^+/H^+$ exchange activity either fail to grow tumours or show severely retarded growth when implanted into immune-deprived mice. It is now evident that NHE1 causes a reversal of the pH gradient in many types of transformed and/or malignant cells so that the intracellular environment is alkaline and the extracellular environment is acidic. This 'malignant acidosis' is considered to represent a key step in oncogenic transformation and is necessary for the development and maintenance of a transformed phenotype.

Additionally, NHE, particularly NHE1, has been implicated in the physiology of several diseases, with the majority of research focusing on the role of NHE1 in heart disease and cancer. In the myocardium, under normal conditions, NHE1 removes excess intracellular acid in exchange for extracellular sodium. The increased intracellular sodium is removed by regulatory membrane proteins, including the $Na^+/K^+$ ATPase and the $Na^+/Ca^{2+}$ exchanger. Problems arise in the myocardium with the increased production of protons that occurs in the human myocardium during and following a myocardial infarction.

The NHE1 isoform is the 'housekeeping' isoform of the exchanger and is ubiquitously expressed in the plasma membrane of virtually all tissues. It is the primary NHE isoform found in the plasma membrane of the myocardium. The NHE2 to NHE5 isoforms are also localized to the plasma membrane, but have more restricted tissue distributions. NHE2 and NHE3 are predominantly located in the apical membrane of epithelia and are highly expressed in kidney and intestine. In contrast thereto, NHE4 is most abundant in stomach, but is also expressed in intestine, kidney, brain, uterus and skeletal muscle, whereas NHE5 is expressed predominantly in brain (but may also be present at low levels in other non-epithelial tissues, including spleen, testis and skeletal muscle). The isoforms NHE6 to NHE9 are ubiquitously expressed and are present in intracellular compartments. These organellar membrane NHEs are presumed to regulate luminal pH and the cation concentration of the intracellular compartments. NHE6 expression is highest in heart, brain and skeletal muscle and is localized to early recycling endosomes. The NHE7 isoform is localized predominantly to the trans-Golgi network, and differs from the other NHE isoforms in that it mediates the influx of either $Na^+$ or $K^+$ in exchange for $H^+$. The highest NHE8 expression is found in skeletal muscle and kidney, and this isoform is mainly localized to the mid- to trans-Golgi compartments. The recently identified NHE9 isoform was found to be localized to late recycling endosomes.

NHEs are targets for inhibition by the diuretic compound amiloride and its analogues, and by benzoylguanidine derivatives. Comparisons of the different NHE isoforms show that they have varying affinities for these inhibitors, with the following order of sensitivity under similar experimental conditions: NHE1≥NHE2>NHE5>NHE3>NHE4. Because NHE1 is the isoform that is most sensitive to inhibition, and seems to be the most important isoform that is present in the plasma membrane of the myocardium, the selective properties of these inhibitors can be exploited therapeutically.

In a preferred embodiment of the present invention the ion channel is an NHE, such as NHE1, NHE2, NH3, NHE4, NHE5, NHE6, NHE7, NHE8 or NHE9, preferably NHE1, NHE2, NHE3 or NHE5, particularly NHE1 or NHE3, especially NHE1.

The NHE1 isoform is the best characterized isoform of the NHE family. NHE1 is 815 amino acids in length, with residues 1 to 500 representing the membrane domain and residues 501 to 815 representing the cytoplasmic tail. The membrane domain of NHE1 is both necessary and sufficient for ion transport, whereas the cytosolic domain is involved in regulation of the activity of the exchanger. Ion flux via the exchanger is driven by the transmembrane $Na^+$ gradient and appears to require no direct metabolic energy input.

As detailed above, the ion channel ligand is preferably an agonist or an antagonist. However, due to the importance of clinical importance of NHE, the ligand is preferably a NHE agonist, more preferably an NHE antagonist. If the ion channel in question is inactive in the absence of a ligand, it may be necessary to monitor the effect of antagonist in the presence of an agonist. In this case, the effect of the antagonist is the inactivation of the agonist-activated ion channel.

In accordance with the present invention a cell is incubated with a ligand and plasma. The cell may be any suitable cell expressing the ion channel in question. Cells expressing the ion channel ligand in question may be cells which naturally express the ion channel. Alternatively, cells may be genetically modified to express the ion channel.

The cell may be isolated (optionally genetically modified), maintained and cultured as known to the skilled person. Aside from temperature and gas mixture, the most commonly varied factor in cell culture systems is the growth medium. Recipes for growth media can vary in pH, glucose concentration, growth factor and the presence of other nutrient components among others. Growth factors used for supplement media are often derived from animal blood such as calf serum. Genetically modified cells may be obtained by inserting the full-length coding sequence of the ion channel, as known to the skilled person. The skilled person in the art knows how to derive a nucleic acid sequence coding for an ion channel protein and how to isolate or produce such a nucleic acid sequence using standard techniques of molecular biology. This can be accomplished, for example, by the use and combination of existing sequences using restriction enzymes. The nucleic acid may be combined with further elements, e.g., a promoter and a transcription start and stop signal and a translation start and stop signal in order to provide for expression of the ion channel's sequence. The resulting nucleic acid sequence may be introduced into cells e.g. using a virus as a carrier or by transfection including e.g. by electroporation, heat shock, magnetofection, nucleofection and the use of transfection agents.

Optionally, the cell may be part of a tissue; however, the method of the invention is an ex vivo method. In a preferred embodiment of the invention the cell is from a cell line (many of which are well characterized and provide for constant conditions and convenient handling), particularly a mammalian cell line, more particularly a human or mouse cell line, especially mouse LTK-cell line LAP1 (Franchi et al., 1986, Proc Natl Acad Sci USA. 83(24): 9388-9392). Examples of suitable cell lines are include but are not limited to HEK 293, 745-A, A-431, BxPC3, C5N, Caco-2, Capan-1, CC531, CFPAC, CHO, CHO K1, COS-1, COS-7, CV-1, EAHY, EAHY 926, F98, GH3, H-295 R, H-4-II-E, HACAT, HACAT A131, HEK, HEL, HeLa, Hep G2, High Five, Hs 766T, HT29, HUV-EC R24, HUV-EC-C, IEC 17, IEC 18, Jurkat, K 562, KARPAS-299, L 929, LIN 175, MAt-LYLU, MCF-7, MNEL, MRC-5, MT4, N64, NCTC 2544, NDCK II, Neuro 2A, NIH 3T3, NT2/D1, P19, SF9, SK-UT-1, ST, SW 480, SWU-2 OS, U-373, U-937, and Y-1. Other suitable cells are those known to the one of skill in the art.

Preferred cell lines are HEK 293 cells (primary human embryonal kidney), 3T3 cells (murine embryonal fibroblasts), CHO cells (Chinese hamster ovary), COS-7 cells (African green monkey cell line), HeLa cells (human epithelioid cervical carcinoma), JURKAT cells (human T-cell leukaemia), BHK 21 cell (hamster normal kidney, fibroblast), and MCF-7 cells (human breast cancer), especially mouse LTK-cell line LAP1.

Within the method of the invention the cell (as defined above) is incubated with an animal's plasma. The animal may be a vertebrate, particularly a mammal, especially a rat, mouse, rabbit, guinea pig, or cat, which provide for safe and convenient handling in the laboratory.

In order to provide for most significant results for human medicine, the plasma may also be derived from a human. For this, venous blood may be obtained by venipuncture from a human donor, wherein usually only a small sample, e.g. 5 ml to 25 ml sample, of blood is adequate for the method of the present invention (see Examples). Blood is most commonly obtained from the median cubital vein, on the anterior forearm (the side within the fold of the elbow). This vein lies close to the surface of the skin, and there is not a large nerve supply. Most blood collection in the industrialized countries is done with an evacuated tube system consisting of a plastic hub, a hypodermic needle, and a vacuum tube.

In accordance with the method of the invention efficiency of an ion channel ligand is determined. Efficiency is determined by determining the effect of the ion channel ligand on the cell in the presence of plasma. As detailed above, the effect on the ligand on the cell may be assessed at each level of signal transduction including binding of ligand to the ion channel, binding of a respective ion to a target, the determination of the amount of a cellular compound such as a second messenger, the determination of the amount of mRNA or a protein, any altered cell function (such as induction of apoptosis or cell circle arrest) etc. Methods of determining binding of a ligand to a target are well known to the skilled person and include those defined herein. Methods for determining the amount of mRNA or protein are also well known to the skilled person. Methods of observing changed cell function largely depend on the type of cell function and are also well known to the skilled practitioner.

The method for determining the effect of an ion channel ligand on a cell may involve a heterogeneous or homogeneous assay. As used herein, a heterogeneous assay is an assay which includes one or more washing steps, whereas in a homogeneous assay such washing steps are not necessary. The reagents and compounds are only mixed and measured. The method of the invention may also include antibodies specific for a ion channel downstream signal. The assay may be an ELISA (enzyme linked immuno sorbent assay), a DELFIA (dissociation enhanced lanthanide fluoro immuno assay), an SPA (scintillation proximity assay) a flashplate assay, a FRET (fluorescence resonance energy transfer) assay, TR-FRET (time-resolved fluorescence resonance energy transfer) assay, a FP (fluorescence polarisation) assay, an ALPHA (amplified luminescent proximity homogenous assay), an EFC (enzyme fragment complementation) assay, a two hybrid assay or a coimmunoprecipitation assay.

In another embodiment of the invention the method for detecting the efficiency may involve measurement one or more second messengers such as cAMP or phospholipid(s), preferably phosphatidyl-inositol-phosphate. The measuring may include the determination of the concentration of one or more second messengers. Means and methods for determining concentrations of one or more second messengers are well known to the skilled person and include such involving e.g. labeled precursors, preferably labeled second messenger precursors (e.g. [$^{32}$P]ATP or [3H]inositol), including purification by e.g. column chromatography, or mass spectrometry. Alteration of phospholipids is usually particularly relevant at calcium channels.

If the ion channel in question, e.g. an NHE or a Sodium-Bicarbonate-Cotransporter, affects the pH value, the effect determined by the method of the present invention is an alteration of the pH-value, preferably an alteration of the intracellular pH-value.

In a preferred embodiment of the invention the effect of the ion channel ligand on the ion channel in question, e.g. an NHE or a Sodium-Bicarbonate-Cotransporter, is determined by fluorescence.

Fluorescence is an optical phenomenon, wherein the molecular absorption of a photon triggers the emission of another photon with a longer wavelength. The energy difference between the absorbed and emitted photons ends up as molecular vibrations or heat. Usually, the absorbed photon is in the ultraviolet range, and the emitted light is in the visible range, but this depends on the absorbance curve and Stokes shift of the particular fluorophore. The number of fluorescence applications is growing in the biomedical biological and related sciences. Methods of analysis in these fields are also growing, albeit with increasingly unfortunate nomenclature in the form of acronyms such as: FLIM, FLI, FLIP, CALI, FLIE, FRET, FRAP, FCS, PFRAP, smFRET, FIONA, FRIPS, SHREK, SHRIMP, TIRF. Most of these techniques rely on fluorescence microscopes. These microscopes use high intensity light sources, usually mercury or xenon lamps, LEDs, or lasers, to excite fluorescence in the samples under observation. Optical filters then separate excitation light from emitted fluorescence, to be detected by eye, or with a (CCD) camera or other light detectors (photomultiplier tubes, spectrographs, etc).

Usually, a fluorescent dye or marker or label is used in order to detect the effect of a signal in question (here the effect of the ion channel ligand). The fluorescent dye comprises a fluorophore. A fluorophore, in analogy to a chromophore, is a component of a molecule which causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. Fluorescein isothiocyanate, a reactive derivative of fluorescein, has been one of the most common fluorophores chemically attached to other, non-fluorescent molecules to create new and fluorescent molecules for a variety of applications. Other historically common fluorophores are derivatives of rhodamine, coumarin and cyanine. Examples fluorescent dyes include without limitation 7-amino-actinomycin D, acridine orange, acridine yellow, Alexa Fluor, AnaSpec, auramine O, auramine-rhodamine stain, benzanthrone, 9,10-bis(phenylethynyl)anthracene, 5,12-bis(phenylethynyl)naphthacene, CFDA-SE, CFSE, calcein, carboxyfluorescein, 1-chloro-9,10-bis(phenylethynyl)anthracene, 2-chloro-9,10-bis(phenylethynyl)anthracene, coumarin, cyanine, DAPI, Dioc6, DyLight Fluor, ethidium bromide, fluorescein, Fura-2, Fura-2-acetoxymethyl ester, green fluorescent protein, Hilyte Fluor, Hoechst stain, Indian yellow, Indo-1, luciferin, perylene, phycobilin, phycoerythrin, phycoerythrobilin, propidium iodide, pyranine, rhodamine, RiboGreen, rubrene, ruthenium(II) tris(bathophenanthroline disulfonate), SYBR Green, stilbene, sulforhodamine 101, TSQ, Texas Red, umbelliferone, yellow fluorescent protein or BCECF.

According to a preferred embodiment, BCECF is used. BCECF (2',7'-Bis-(carboxyethyl)-5(6)-carboxyfluorescein, C27H20O11), M=520,45 g/molCAS-Nr.: 85138-49-4, storage: 2 to 8° C., sheltered from light) BCECF is an analogon of Carboxyfluorescein with improved characteristics for pH determination in lymphocytes due to its enhanced retention inside of the cells. For efficient uptake into intact cells BCECF can be used in the form of the acetoxymethylester BCECF/AM, which is cleaved inside the cells to form the more impermeable BCECF. The maximum of excitability for a 70 nM solution of BCECF lies at 500 nm. The intensity of fluorescence of BCECF can be influenced by several agents, e.g.: glycerol, saccharose, polyethylenglycol or polyvinylpyrrolidon. A suitable concentration of BCECF is 5 µM (final concentration).

In the context of the present invention the fluorescent dye is sensitive for the effect of the ion channel ligand on the ion channel. The effect may be a direct effect on the channel itself (e.g. conformational change, change in binding characteristics etc.) or a change in the signaling pathway downstream the ion channel in question, particularly a chance in the intracellular concentration of the ion transported by the ion channel in question. The ion may be, for example, $H^+$, $HCO_3^-$, $K^+$, $Na^+$, $Cl^-$ or $Ca^{2+}$. Suitable pH-dependent fluorescent markers (for $H^+$ and $HCO_3^-$) include without limitation the $H^+$-selective fluorescent chromoionophore ETH 5294, S NAFL, SNARF, HPTS, fluoresceins, carbofluoresceins, BCECF (2',7'-bis(2-carboxyethyl) 5(and 6)carboxyfluorescein) and BCPCF (2',7'-bis(2-carboxypropyl)-5(and 6)carboxyfluorescein). Calcium ions may be detected by using aequorin (the first photoprotein to be isolated), calmodulin labeled with Alexa-488 or photina (Axxam SpA, Milan, Italy), Fluo4 (Glycine, N-[4-[6-[(acetyloxy)methoxy]-2,7-difluoro-3-oxo-3H-xanthen-9-yl]-2-[2-[2-[bis[2-[(acetyloxy)methoxy]-2-oxoethyl]amino]-5-methylphenoxy]ethoxy]phenyl]-N-[2-[(acetyloxy)methoxy]-2-oxoethyl]-, (acetyloxy)methyl ester, C51H50F2N2O23), M=1096.95 g/molCAS-Nr.: 273221-67-3, storage: 2 to 8° C., sheltered from light) or Fura2 (5-Oxazolecarboxylic acid, 2-(6-(bis(2-((acetyloxy)methoxy)-2-oxoethyl)amino)-5-(2-(2-(bis(2-((acetyloxy)methoxy)-2-oxoethyl)amino)-5-methylphenoxy)ethoxy)-2-benzofuranyl)-(acetyloxy)methyl ester, C44H47N3O24), M=1001.86 g/molCAS-Nr.: 108964-32-5, storage: −20° C., sheltered from light). For the detection of sodium and potassium ions ionophore X and ionophore BME-44 may be employed.

Such methods may be carried out as follows, wherein the following is for illustrative purposes only. The skilled person will understand that one or more steps may be carried out in a different manner (e.g. as detailed in the present description of the invention):

Cells may be obtained by isolation from tissues for ex vivo culture. For example, pieces of tissue can be placed in growth media, and the cells that grow out are available for culture. This method is known as explant culture. Alternatively a cell line (e.g. an established or immortalised cell line) may be used. There are numerous well established cell lines representative of particular cell types (see also above).

Cells may be cultured in a suitable medium (e.g. commercially available medium including serum and antibiotics). Cells are usually cultured in a suitable atmosphere (e.g. 5% $CO_2$), relative humidity (e.g. 90%) and temperature (e.g. at 37° C.). For high-through-put screening and/or convenient handling cells may be cultivating in multiwell plates such as 96 well plates, 24 well plates etc.

As detailed above, intracellular pH change may be determined using fluorescent markers. Suitable markers include SNARF-1, BCECF and CMFDA. Excitation and emission are Exc 485, Em 590 nm for carboxy SNARF-1; Exc 500, Em 538 nm for BCECF; and Exc 485, Em 538 nm for CMFDA. Excitation and emission bandwidths may be 20 nm and 25 nm, respectively. A suitable device for measuring intracellular pH is for example FLUOstar 97 fluorometer multi-well plate reader (BMG LabTechnologies, Inc, Durham, N.C.) or the device described in the Examples.

According to one embodiment the fluorescent dye BCECF is used (2',7'-Bis-(carboxyethyl)-5(6)-carboxyfluorescein, C27H20O11), M=520,45 g/molCAS-Nr.: 85138-49-4, storage: 2 to 8° C., sheltered from light) BCECF is an analogon of Carboxyfluorescein with improved characteristics for pH determination in lymphocytes due to its enhanced retention inside of the cells. For efficient uptake into intact cells BCECF can be used in the form of the acetoxymethylester BCECF/AM, which is cleaved inside the cells to form the more impermeable BCECF. The maximum of excitability for a 70 nM solution of BCECF lies at 500 nm. The intensity of fluorescence of BCECF can be influenced by several agents, e.g.: glycerol, saccharose, polyethylenglycol or polyvinylpyrrolidon. A suitable concentration of BCECF is 5 µM (final concentration).

The following is one examplary procedure for the prepararation of cells for intracellular pH determination: Cells may be grown to e.g. 90% confluence, harvested with e.g. trypsin, and immediately quenched with culture medium containing e.g. 10% fetal bovine serum, pelleted, and then rinsed once. Pelleted cells may be resuspended in fresh medium, allowed to recover (e.g. under 5% $CO_2$ at 37° C. for 1 hour), rinsed e.g. twice with e.g. bicarbonate-free buffer (such as 130 mM NaCl, 4.7 mM KCl, 1.2 mM $MgSO_4$, 1.2 mM $KH_2PO_4$, 11.7 mM D-glucose, 1.3 mM $CaCl_2$, 10 mM HEPES, pH 7.4) and then loaded with the above marker (dye). According to another embodiment, the cells are not trypsinized prior to dye-loading.

Dye loading may e.g. be performed as follows: cells are incubated with 5 µM 5-(and-6)-carboxy SNARF-1/AM (Molecular Probes, Eugene, Oreg.) for 30 minutes at room temperature in bicarbonate-free Krebs-Hepes buffer (pH 7.4) containing 1% (wt/vol) Pluronic F-127 (Sigma Chemicals, St Louis, Mo.). Cells can e.g. be loaded with 1 µM 2-,7-bis-(2-carboxyethyl)-5-(and-6)-carboxyfluorescein (BCECF/AM) (Molecular Probes) for 45 minutes at room temperature in buffer. Cells can be loaded with 5 µM CellTracker Green CMFDA (5-chloromethylfluorescein diacetate) (Molecular Probes) for 45 minutes at 37° C. in buffer. The loading with one or more of the other above-identified dyes can be performed similarly, according to appropriate and well known protocols.

After loading, cells can e.g. be rinsed one or more time (e.g. twice) with buffer and resuspended in fresh medium, and are allowed to recover under 5% $CO_2$ at 37° C. for 1 hour or longer (e.g. overnight). After dye loading and recovery time, the cells can be rinsed one or more (e.g. 3) times with an appropriate buffer, e.g. bicarbonate-free Krebs-Hepes buffer (pH 7.4 or 6.0), resuspended to a final concentration of 2.5× $10^6$ cells/mL and held at 4° C.

The cells can be diluted and distributed evenly (approximately 35 000 cells/well) into an opaque white 96-well plate (or any other suitable plate, e.g. black with transparent bottom). Plasma and buffer alone or buffer containing ligand can be injected sequentially into separate wells and the fluorescence intensity recorded at appropriate (e.g. 20 second) intervals. Several (e.g. five) baseline readings can be taken at appropriate intervals (e.g. 20-second intervals) prior to each injection.

At the end of each experiment, an in situ calibration procedure with a known ion channel ligand (e.g nigericin for $H^+/K^+$ exchanger) may be used to relate the fluorescence intensities to pH value. This may e.g. be done in that the $K^+/H^+$ exchanger ionophore sets $[K^+]o=[K^+]i$ and pHo=pHi by exposing the cells to different pH buffers in a depolarizing high $K^+$ buffer (140 mM KCl, 1.2 mM $MgSO_4$, 1.2 mM $KH_2PO_4$, 11.7 mM D-glucose, 1.3 mM $CaCl_2$, 10 mM HEPES, pH 6.0 to pH 8.0, in the presence of 20 µM nigericin). To correct for small variations in cell density and instability of illumination intensity between the calibration and the experiments, the CMFDA concentration was measured by permeabilizing the cells at the end of each experiment with 0.1% Triton X-100, and adjusting the pH to 11 with KOH.

Additionally, dye leakage may be followed by separating the contributions from leaked and intracellular dye. For this, at different time intervals, cells may be spun down e.g. for 30 seconds. Then, the fluorescence intensity of each supernatant and resuspended cell lysate solutions may be measured. Fluorescence intensity of supernatant solutions reflects dye leakage from the cells, and the combined fluorescence intensity from both supernatant and cell lysate may be used to define total amount of dye. Fluorescence intensity of controls (no dye) may be subtracted from each fraction, and leakage may be reported as the ratio of fluorescence intensity (supernatant/total) versus time.

A further exemplary method is described in the Examples.

Alternatively, ion-sensitive microelectrodes (including an ion-selective ionophore such as the sodium-ionophore Bis (12-crown-4), the potassium-selective ionophor Bis(benzo-15-crown-5), the calcium-selective ionophore HDOPP-Ca) or ion sensitive enzymes (such as potassium-dependent urea amidolyase, pyruvate kinase (U.S. Pat. Nos. 5,501,958 and 5,334,507) or glycerol dehydrogenase (U.S. Pat. No. 5,719, 036)) may be used for the detection of ion flux across cell membranes. Further pH-sensitive methods include distribution of weak acids or bases, $^{31}$P-NMR spectroscopy and pH-sensitive Green fluorescent protein [GFP].

Preferably, the method is adapted for high-through put screening. In this method a large number of compounds is screened against the ion channel in question in whole-cell assays. Typically, these screenings are carried out in 96 well plates using automated, robotic station based technologies or in higher-density array ("chip") formats.

In one embodiment of the method of the invention the ion channel ligand, such as the NHE ligand, is administered to the cell together with the plasma. This may be achieved by administering the ligand to a (non-human) animal. The ligand may be administered by in any suitable route, including parenteral (such as intravenous, intraarterial, intramuscular, intracardiac, subcutaneous, intradermal, intrathecal intraperitoneal), enteral (such as oral or rectal), topical (such as epicutaneous, inhalational, nasal or vaginal) etc. Administration via feed is preferred.

After an amount of time sufficient to allow the ligand to be present in the plasma, plasma is taken from the animal. In order to carry out the method of the invention the plasma including the ligand is added to cell and the effect of the ligand on the cell is determined. The determination of the effect may include the determination of the concentration of the ligand in the plasma (see also Example 2). If the amount of ligand administered to the animal is compared to that present in the plasma, conclusion on e.g. the extent and rate of absorption, distribution, metabolism and excretion of the ligand may be draw from the comparison.

In accordance with the present invention, the method for determining the effect of an ion channel ligand may be used to determine plasma concentration of a ligand. This may be accomplished by comparing the effect of plasma with unknown ligand concentration to a standard, e.g. a standard curve (see e.g. Example 2).

The method of the invention may be used for screening for a medicament for preventing and/or treating a disease involving ion channel dysfunction, particularly for preventing and/ or treating a cardiovascular disease or cancer. If used for screening purposes the ligand tested may be either a known ion channel ligand or substance, the function of which is still unknown or not yet related to the ion channel. Accordingly, the method may be used for the identification of new ion channel ligand. Alternatively, known ion channel ligands may be tested for their efficiency using the method of the invention. The efficiency may be compared to the ligands action in a plasma-free system (such as the binding affinity) in order to assess the effect of the plasma on the activity of the ligand and to estimate the in vivo activity of the ligand.

The ligand may be provided in the form of a chemical compound library. Chemical compound libraries include are plurality of chemical compounds and have been assembled from any of multiple sources, including chemically synthesized molecules and natural products, or have been generated by combinatorial chemistry techniques. They are especially suitable for high throughput screening. They may be comprised of chemical compounds of a particular structure or compounds of a particular creature such as a plant. In the context with the present invention the chemical compound library is preferably a library comprising small molecules.

In the following, the present invention is illustrated by figures and examples which are not intended to limit the scope of the present invention.

FIGURES

EXAMPLES

Example 1

Figure 1:
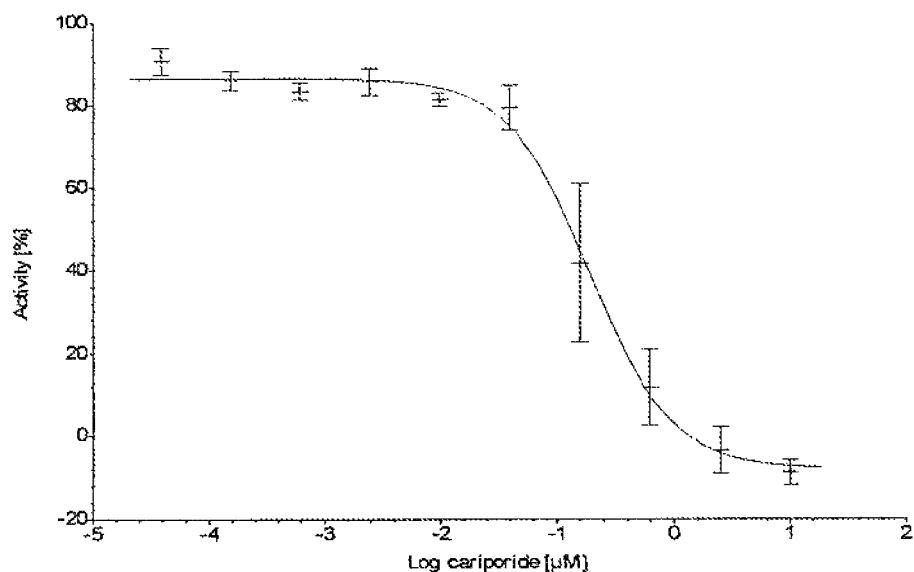
FIG. 1 shows cariporide calibration curve of the calculated efficiency in rat plasma ($EC_{50}$=115 nM).

Establishing an Assay to Determine the Effective Concentration of NHE Antagonists in Animal Plasma Samples Plasma samples were obtained from male New Zealand rabbits (2.5-3.5 kg) maintained on standard rabbit chow with 0.3% cariporide (NHE inhibitor). A blood sample was taken after 1 week from the auricular artery for the determination of the plasma concentrations of cariporide. Determination of plasma concentration of cariporide was done as described below:

The NHE-Gene (SLC9A1, Franchi A. et al., Proc Natl Acad Sci USA., 1986 December; 83(24):9388-92.) was cloned into the pMamneo-vector and introduced into LAP1 (mouse LTK-cell line) cells. Stable cell lines were generated from transfected cells.

LAP1 (mouse LTK-cell line) cells stably expressing human NHE1 (hNHE1) were seeded with a density of 25.000 cells/well/100 µl medium (Iscove-medium, 10% FCS, 2 mM L-glutamine, 100 u/ml penicilline/streptomycine, 50 µg/ml gentamicine, 400 µg/ml G418) on black, clear bottom 96-well microplates (Costar®, Corning Inc., Corning, N.Y.). Cells were incubated overnight at 37° C., 5% $CO_2$ and 90% humidity. The medium was discarded prior to measurement and 100 µl/well dye buffer (20 mM HEPES, pH 7.4 adjusted with KOH, 20 mM $NH_4Cl$, 115 mM choline chloride, 1 mM $MgCl_2$, 1 mM $CaCl_2$, 5 mM KCl, 5 mM glucose, 5 µM BCECF) were added. After incubation for 20 min at 37° C. the cells were washed 3-times with $Na^+$-free washing buffer (5 mM HEPES, pH 7.4 adjusted with KOH, 133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM glucose), leaving 90 µl of washing buffer per well. pH-recovery was measured with a FLIPR (Fluorometric Imaging Plate Reader, Molecular Devices, Sunnyvale, Calif.; laser power 0.3 W, aperture 4, measuring interval 2 s, time of measurement 120 s). During measurement 90 µl of plasma solution (90% animal plasma from animals feeded w/o antagonist, 10% $Na^+$-buffer: 10 mM HEPES, pH 7.4 adjusted with KOH, 133.8 mM NaCl, 4.7 mM KCl, 1.25 mM $MgCl_2$, 1.25 mM $CaCl_2$, 0.97 mM $Na_2HPO_4$, 0.23 mM $NaH_2PO_4$, 5 mM glucose) were added to the wells. Due to the $Na^+$ in the buffer NHE1 starts to transport $H^+$ out of the cells, leading to an increase in intracellular pH and fluorescence. High control: plasma solution without antagonist. Low control: plasma solution with 20 µM cariporide (10 µM final concentration). Cariporide was added to the plasma after preparation. Addition of 10 µM cariporide leads to a complete block of NHE1 activity. For calibration different amounts of cariporide and the tested antagonists were added to plasma after preparation to determine the efficiency in animal plasma.

For calculation of NHE1 activity, the increase in fluorescence between the $12^{th}$ and $32^{nd}$ s was calculated. The high control was set as 100% activity whereas the low control determines 0% NHE1 activity. %-activity of the samples was calculated by a comparison to the controls.

TABLE 1

Plasma assay example with plasma derived from rabbits.

|  | Average | SD |
|---|---|---|
| Low control | 631 | 416 |
| High control | 14416 | 875 |
| z' | 0.74 | |

Fluorescence increase measured between the $12^{th}$ and $32^{nd}$ s. Low control: Plasma with 10 μM cariporide. High control: Plasma. Z' > 0.5 indicates a very good assay performance.

TABLE 2

NHE1-activity with plasma derived from rabbits with 0.3% cariporide chow

|  | Activity [%] | SD |
|---|---|---|
| Rabbit #1 | −5.45 | 1.30 |
| Rabbit #2 | −1.53 | 1.10 |
| Rabbit #3 | −0.39 | 0.55 |
| Rabbit #4 | −2.25 | 4.09 |
| Rabbit #5 | −0.63 | 0.74 |
| Rabbit #6 | −5.45 | 1.30 |

Values were calculated in comparison to the controls. All rabbits have sufficient cariporide in the plasma to block NHE1 activity completely.

Results: As shown in Tables 1 and 2, the example showed good results. The assay performance was very good (z'=0.74, Table 1). All probes showed complete block of NHE1 indicating a cariporide concentration ≥10 μM (Table 2, FIG. 1).

Example 2

Assay to Determine the Plasma Levels of NHE Antagonists

The animals used for the plasma studied were pretreated as follows:
Animals: Male Sprague Dawley rats (Moellegard)
Body weight: 320-360 g
Anesthesia: Thiopental-Na (Trapanal 100 mg/kg i.p.)
Respiration: 40 Vol % $O_2$
Blood gases: 32-40 mmHg $pCO_2$
 80-100 mmHg $PO_2$
 pH 7.35-7.49
 SaO2>96%
Ischemia: 20 min occlusion of LAD (left anterior descending coronary artery)
Reperfusion: 60 min
Body temperature: 36.5° C.
Measurement parameters: myocardial infarct mass mean
 arterial blood pressure heart rate
 compound plasma levels
Blood samples: single probe, 85 min after i.v. injection (end of reperfusion)
 or
 single probe 200 min after oral treatment (end of reperfusion)

| 0. | vehicle 1 ml/kg i.v. saline (n = 8) | 5 min before occlusion |
| I. | Cariporide 1 mg/kg i.v. (n = 8) | 5 min before occlusion |
| II. | compound X 3 mg/kg i.v. (n = 8) | 5 min before occlusion |
| III. | compound X 1 mg/kg i.v. (n = 8) | 5 min before occlusion |
| IV. | compound X 0.3 mg/kg i.v. (n = 8) | 5 min before occlusion |
| V. | compound X 3 mg/kg p.o. (n = 8) | 5 min before occlusion |
| VI. | compound X 10 mg/kg p.o. (n = 8) | 5 min before occlusion |
| VII. | compound X 0.1 mg/kg i.v. (n = 8) | 5 min before occlusion |

Groups:

Different amounts of plasma were prepared from groups I to VII 85 mins after injection (groups I-IV, VII) or 200 mins after treatment (groups V-VI) and from untreated rats. Plasma was stored at −20° C. until the analysis was performed.

For the cell-based determination of NHE1 ligand efficiency, LAP1 (mouse LTK-cell line) cells stably expressing hNHE1 (see Example 1) were seeded at a density of 25.000 cells/well/100 μl medium (Iscove-medium, 10% FCS, 2 mM L-glutamine, 100 μ/ml penicilline/streptomycine, 50 μg/ml gentamicine, 400 μg/ml G418) on black, clear bottom 96-well microplates (Costar®, Corning Inc., Corning, N.Y.). Cells were incubated overnight at 37° C., 5% $CO_2$ and 90% humidity. The medium was discarded prior to measurement and 100 μl/well dye buffer (20 mM HEPES, pH 7.4 adjusted with KOH, 20 mM $NH_4Cl$, 115 mM choline chloride, 1 mM $MgCl_2$, 1 mM $CaCl_2$, 5 mM KCl, 5 mM glucose, 5 μM BCECF) were added. After incubation for 20 min at 37° C. the cells were washed 3-times with $Na^+$-free washing buffer (5 mM HEPES, pH 7.4 adjusted with KOH, 133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM glucose), leaving 90 μl of washing buffer per well. The plasma probes were prepared as followed: 10% (v/v) $Na^+$-buffer (10 mM HEPES, pH 7.4 adjusted with KOH, 133.8 mM NaCl, 4.7 mM KCl, 1.25 mM $MgCl_2$, 1.25 mM $CaCl_2$, 0.97 mM $Na_2HPO_4$, 0.23 mM $NaH_2PO_4$, 5 mM glucose) were added to 90% (v/v) rat plasma.

High controls (plasma solution without antagonist) and low controls (plasma solution with 20 μM cariporide, 10 μM final concentration) were prepared. A dilution series of cariporide and COMPOUND X in 10% (v/v) $Na^+$-buffer/90% (v/v) rat plasma was used for a calibration curve to calculate the compound concentration in the rat plasma probes FIGS. 1 and 2).

The pH-recovery was measured with a FLIPR (Fluorometric Imaging Plate Reader, Molecular Devices, Sunnyvale, Calif.; laser power 0.3 W, aperture 4, measuring interval 2 s, time of measurement 120 s). During measurement 90 μl of plasma solution were added to the wells.

For calculation of NHE1 activity, the increase in fluorescence between the $12^{th}$ and $32^{nd}$ s was calculated. The high control was set as 100% activity and the low control as 0% NHE1 activity. Activity (%) of the samples was calculated by a comparison of the controls. Compound plasma levels were calculated in relation to the calibration curve.

Results: The results are summarized in Table 3. The z' factor was greater than 0.75 for all measurements.

TABLE 3

NHE1-Activity with plasma derived from rat treated as described above.

| Probe set | Compound | Medication | rel. $F_I$ increase mean | SD | Activity [%] mean | SD |
|---|---|---|---|---|---|---|
| High | — | — | 13543 | 2329 | 100 | — |
| Low | cariporide | — | 3110 | 301 | 0 | — |
| I | cariporide | 1 mg/kg i.v. | 7392 | 1625 | 49.95 | 18.06 |
| II | compound X | 3 mg/kg i.v. | 6067 | 919 | 35.23 | 10.22 |
| III | compound X | 1 mg/kg i.v. | 8223 | 1300 | 59.19 | 14.45 |
| IV | compound X | 0.3 mg/kg i.v. | 13337 | 1429 | 84.38 | 12.04 |
| V | compound X | 10 mg/kg p.o. | 6301 | 1579 | 25.09 | 13.31 |
| VI | compound X | 3 mg/kg p.o. | 9208 | 1909 | 49.59 | 16.09 |
| VII | compound X | 0.1 mg/kg i.v. | 12193 | 1580 | 87.51 | 9.36 |

Activities were calculated from the relative fluorescence increase in comparison to the controls. The eight probes per group were averaged.

Figure 2:
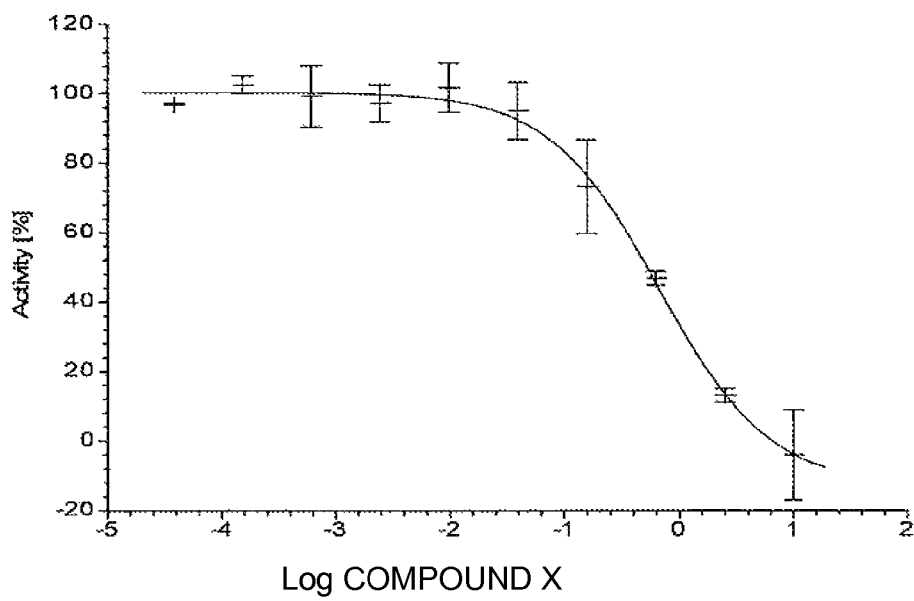
FIG. 2 shows the calibration curve for a novel compound X of the calculated efficiency in rat plasma ($EC_{50}$=662 nM).

The exemplary calibration curves for cariporide and compound X are shown in FIGS. 1 and 2.

Additionally, calibration curves were used to calculate the compound plasma levels in the probe sets. The calibration curves were calculated using following formula:

$$f(x) = A + \left( \frac{B - A}{1 + \left(\frac{C}{x}\right)^D} \right) \quad (1)$$

The variables were set as shown in table 4:

TABLE 4

Fit parameters used to calculate the calibration curves.

| | cariporide | COMPOUND X |
|---|---|---|
| A | −7.947 | −12.752 |
| B | 86.547 | 100.146 |
| C | 0.189 | 0.662 |
| D | −1.239 | −0.9138 |

The compound plasma levels were calculated from activity (Table 4) using formula 2. The results were multiplied by two because of the dilution of the plasma probes.

$$x = \frac{C}{\sqrt[D]{\frac{B-A}{Y-A}}} \quad (2)$$

Figure 3:
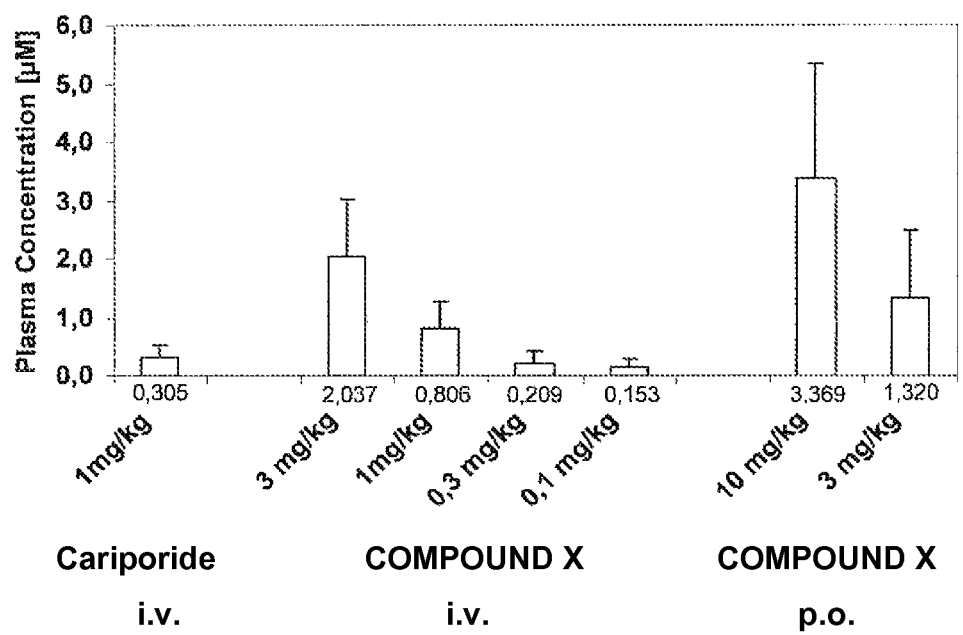
FIG. 3 shows estimated plasma concentration of cariporide and compound X using the NHE1 in vitro assay.

The calculated plasma compound levels are shown in FIG. 3.

Accordingly, it is possible to determine the efficacy of NHE1 inhibitors in rat plasma using the NHE1 assay of the present invention. It is also possible to calculate the active plasma concentration of these compounds according to the calibration curves. The NHE1 inhibitors were active in rat plasma after preparation. The data show a good dose dependency of NHE1 inhibition.

The invention claimed is:

1. A method for determining the in vivo efficiency of a sodium-proton-exchanger (NHE) ion channel ligand comprising the steps of:
   a) contacting a cell expressing a sodium-proton-exchanger (NHE) ion channel in vitro with either
      i) plasma of an animal and the ion channel ligand, or
      ii) the plasma of an animal which has been administered the ion channel ligand;
   b) determining the effect of the ion channel ligand on the cell
   c) determining ion channel ligand availability by comparing the ligand concentration in the plasma to the concentration of ligand administered; and
   d) correlating the effect of the ion channel ligand on the cell with the ligand availability to determine the in vivo efficiency of the ligand.

2. The method of claim 1, wherein the NHE is NHE1, NHE2, NHE3 or NHE5.

3. The method of claim 1, wherein the ion channel ligand is an agonist or an antagonist.

4. The method of claim 1, wherein the cell is a cell line.

5. The method of claim 1, wherein the animal is a vertebrate.

6. The method of claim 1, wherein the animal is a human.

7. The method of claim 1, wherein the effect is an alteration of a pH-value.

8. The method of claim 7, wherein the effect is an alteration of the intracellular pH-value.

9. The method of claim 1, wherein the effect is determined by fluorescence.

10. The method of claim 1, wherein the NHE ligand has been administered the animal, wherein the animal is to a non-human animal.

11. The method of claim 1, wherein the method is used for screening for a medicament for treating a disease involving ion channel dysfunction.

12. The method of claim 1, wherein the method is used for screening for a medicament for preventing and/or treating a cardiovascular disease or cancer.

13. The method of claim 4, wherein the cell line is a mammalian cell line.

14. The method of claim 13, wherein the cell line is a human cell line.

15. The method of claim 13, wherein the cell line is a mouse cell line.

16. The method of claim 15, wherein the cell line is a mouse LTK cell line.

17. The method of claim 5, wherein the vertebrate is a mammal.

18. The method of claim 17, wherein the mammal is selected from the group consisting of rat, mouse, rabbit, guinea pig and cat.

* * * * *